United States Patent

Sumiya

[11] Patent Number: 5,562,656
[45] Date of Patent: Oct. 8, 1996

[54] OPHTHALMIC APPARATUS

[75] Inventor: Toshifumi Sumiya, Nukata-gun, Japan

[73] Assignee: Nidek Co., Ltd., Japan

[21] Appl. No.: 90,611

[22] Filed: Jul. 12, 1993

[30] Foreign Application Priority Data

Jul. 31, 1992 [JP] Japan ................................ 4-224893

[51] Int. Cl.$^6$ ................................ A61B 3/10; A61F 9/06
[52] U.S. Cl. ................................ 606/4; 351/214; 606/11
[58] Field of Search ................................ 606/4, 5, 6, 10, 606/11, 12, 13, 14; 351/205, 211, 214, 221

[56] References Cited

U.S. PATENT DOCUMENTS

| | | | |
|---|---|---|---|
| 4,711,541 | 12/1987 | Yoshino et al. | 606/4 |
| 4,900,145 | 2/1990 | Akiyama | 351/205 |
| 5,120,123 | 6/1992 | Akiyama | 351/221 |
| 5,177,512 | 1/1993 | Abe et al. | 351/221 |
| 5,250,965 | 10/1993 | Abe et al. | 351/221 |
| 5,321,447 | 6/1994 | Sander et al. | 351/205 |

*Primary Examiner*—Angela D. Sykes
*Assistant Examiner*—Sonya Harris-Ogugua
*Attorney, Agent, or Firm*—Rossi & Associates

[57] ABSTRACT

An ophthalmic apparatus for measuring and operating a subject's eye, which includes an ophthalmic operation apparatus, provides an alignment mechanism including a slit image projecting system for projecting an alignment slit image on the subject's eye, a slit image observing system for observing the slit image projected on the subject's eye, wherein a plurality of the slit image projecting system are arranged so as to project the slit image from at least two directions on the subject's eye, the directions putting the optical axis of the slit image observing system therebetween, and an alignment moving device by which an apparatus body including the slit image observing system is moved relatively to the subject's eye in three-dimensional direction.

11 Claims, 6 Drawing Sheets

FIG. 6
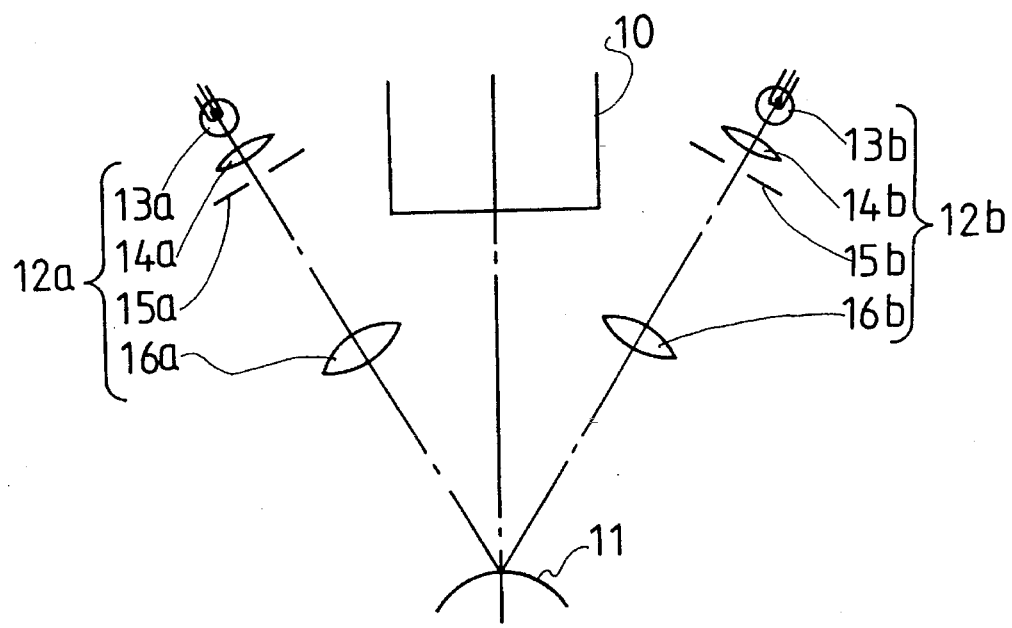
FIG. 7(a)     FIG. 7(b)     FIG. 7(c)
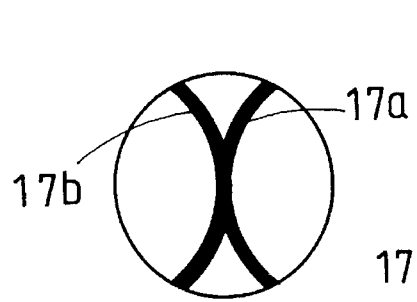 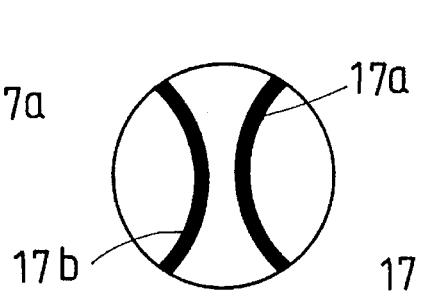 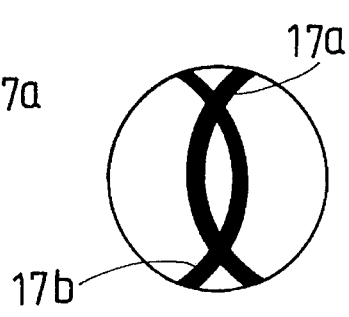

OPHTHALMIC APPARATUS

BACKGROUND OF THE INVENTION

1. Field of the Invention

The present invention relates to an ophthalmic apparatus, and more particularly to an alignment mechanism of the ophthalmic apparatus for aligning an operation apparatus and a measuring apparatus with a patient's eye.

2. Description of Related Art

FIG. 1 shows a typical alignment mechanism used in a known ophthalmic operation apparatus and a known measuring apparatus.

In the alignment mechanism, which provides a light source 2 arranged at the oblique above position of an examinee's eye 1, lenses 3, 4 and a light detector 5, a light beam emitted from the light source 2 is condensed through the lens 3 on an apex of cornea of the examinee's eye 1, and reflected thereon. The reflected light is again focused through the lens 4 toward the light detector 5 arranged at a focus position of the lens 4, and detected thereby.

This alignment method, although being able to obtain satisfactory alignment precision thereby, has only a very limited detectable scope. Accordingly, the alignment light may be focused out of the light detector 5 if the position (of the apparatus) is even slightly dislocated.

In addition to the above problem, this alignment method needs a display means to display a detected result by the light detector 5 on an observing system including a microscope or a TV monitor or the like, whereby the alignment mechanism may become complicated.

Another alignment mechanism shown in FIG. 2 has also been proposed. In the alignment mechanism, lasers 6a and 6b are arranged respectively at right and left oblique above positions of an examinee's eye 1. The respective laser beams emitted from the two lasers 6a and 6b irradiate the examinee's eye 1 and form laser spots thereon, the laser spots are then observed through an observing system 7 arranged on the optical axis of the examinee's eye 1. Thus, the alignment is adjusted so as to correspond the laser spots each other on the examinee's eye 1, namely, the focus position (alignment) is correct when laser spots by the two lasers 6a and 6b become one laser spot 8 as shown in FIG. 3(a), the examinee's eye 1 is too near than a proper focus position when two laser spots 8a and 8b are separate spots as shown in FIG. 3(b), and the examinee's eye 1 is too far than a proper focus position when two laser spots 8a and 8b are changed places with each other as shown in FIG. 3(c).

The alignment method needs corresponding two small laser spots formed on the examinee's eye, however, the reflected plane on which the light beams are reflected toward the observing system is the curved cornea surface of the examinee's eye. Accordingly the small spots are even difficult to observe. And further, when the examinee's eye 1 is positioned either too near (b) or far (c) than a proper focus position, the operator may observe the two spots in a same view, thereby can not judge whether a distance between the examinee's eye and the apparatus is too short or long to determine an alignment direction to which the apparatus should be moved.

SUMMARY OF THE INVENTION

The present invention has been made in view of the above circumstances and has an object to overcome the above problems and to provide an ophthalmic apparatus provided with an alignment mechanism capable of easily aligning the apparatus with the examinee's eye by a simple construction.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic apparatus of this invention comprises an alignment mechanism including a slit image projecting system for projecting an alignment slit image on the subject's eye, a slit image observing system for observing the slit image projected on the subject's eye, wherein a plurality of the slit image projecting system are arranged so as to project the slit image from at least two directions on the subject's eye, the directions putting the optical axis of the slit image observing system therebetween, and an alignment moving means for moving an apparatus body comprising the slit image observing system, relatively to the subject's eye, in three-dimensional direction.

In the second aspect of the present invention, an ophthalmic operation apparatus comprises an operation laser source, an operation laser optical system for projecting an operation laser beam emitting from the laser source on the patient's eye, a pair of slit image projecting systems, each for projecting an alignment slit image on the patient's eye, a slit image observing system for observing a slit image projected on the patient's eye through the slit image projecting system, and an alignment moving means for moving the operation laser optical system, relative to the patient's eye, in three-dimensional direction, based on the slit image on the patient's eye observed through the slit image observing system.

According to the present invention, an alignment for the apex of a cornea can be easily achieved with a simple mechanism in which two slit light beams are projected from oblique above positions on the cornea and the operator adjusts the alignment based on the slit image observed by the observing system.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

FIG. 6 is a schematic diagram of explaining an alignment mechanism of the present invention;

FIGS. 7(a) through 7(c) are diagrams of showing various alignment conditions in the optical axis direction according to the present invention;

DETAILED DESCRIPTION OF THE PREFERRED EMBODIMENTS

A detailed description of one preferred embodiment of an ophthalmic apparatus embodying the present invention will now be given referring to the accompanying drawings.

Figure 1:
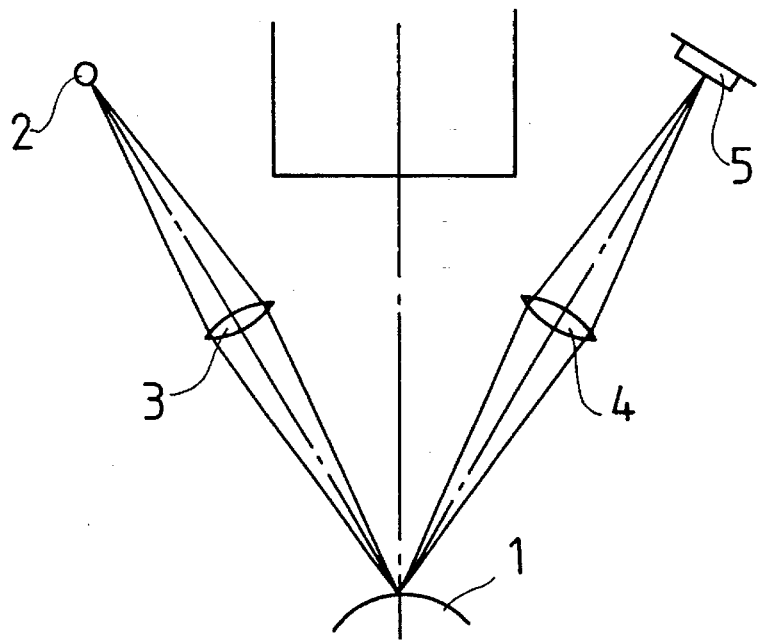
FIG. 1 is a schematic diagram of explaining an alignment mechanism of a prior art.
Figure 2:
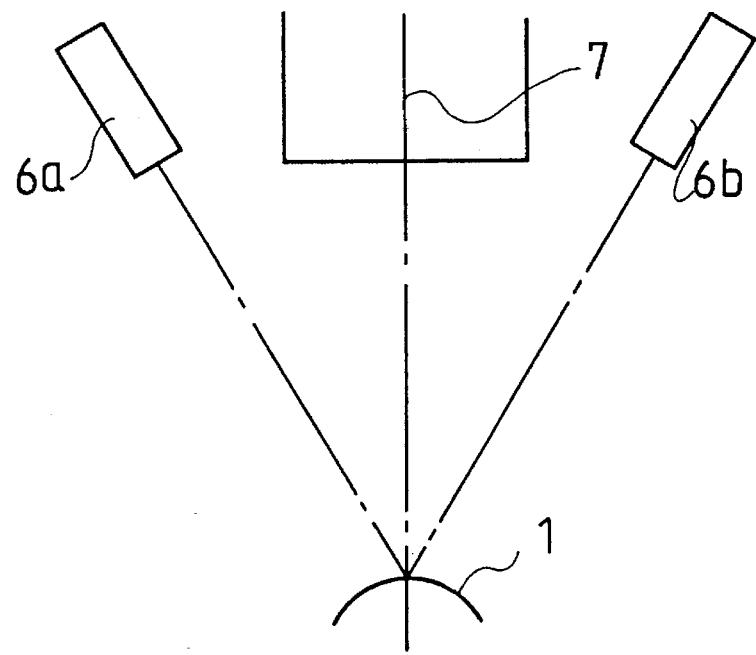
FIG. 2 a schematic diagram of explaining an alignment mechanism of another prior art.
Figure 3:
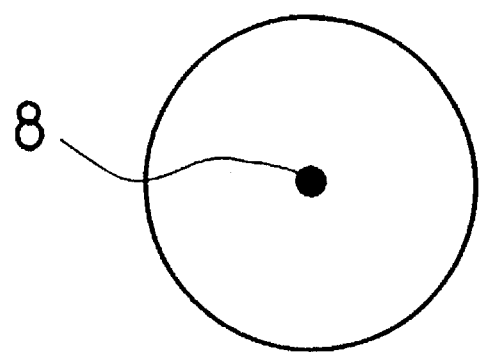
FIGS. 3(a) through 3(c) are diagrams of showing various alignment conditions in a case of using the alignment mechanism of FIG. 2.
Figure 3:
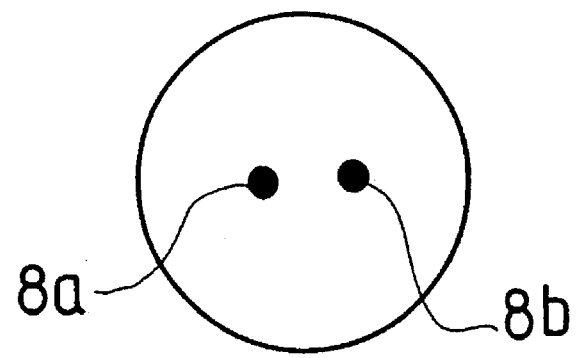
Figure 3:
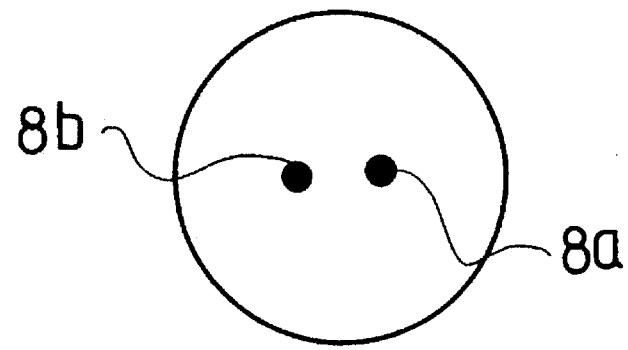
Figure 4:
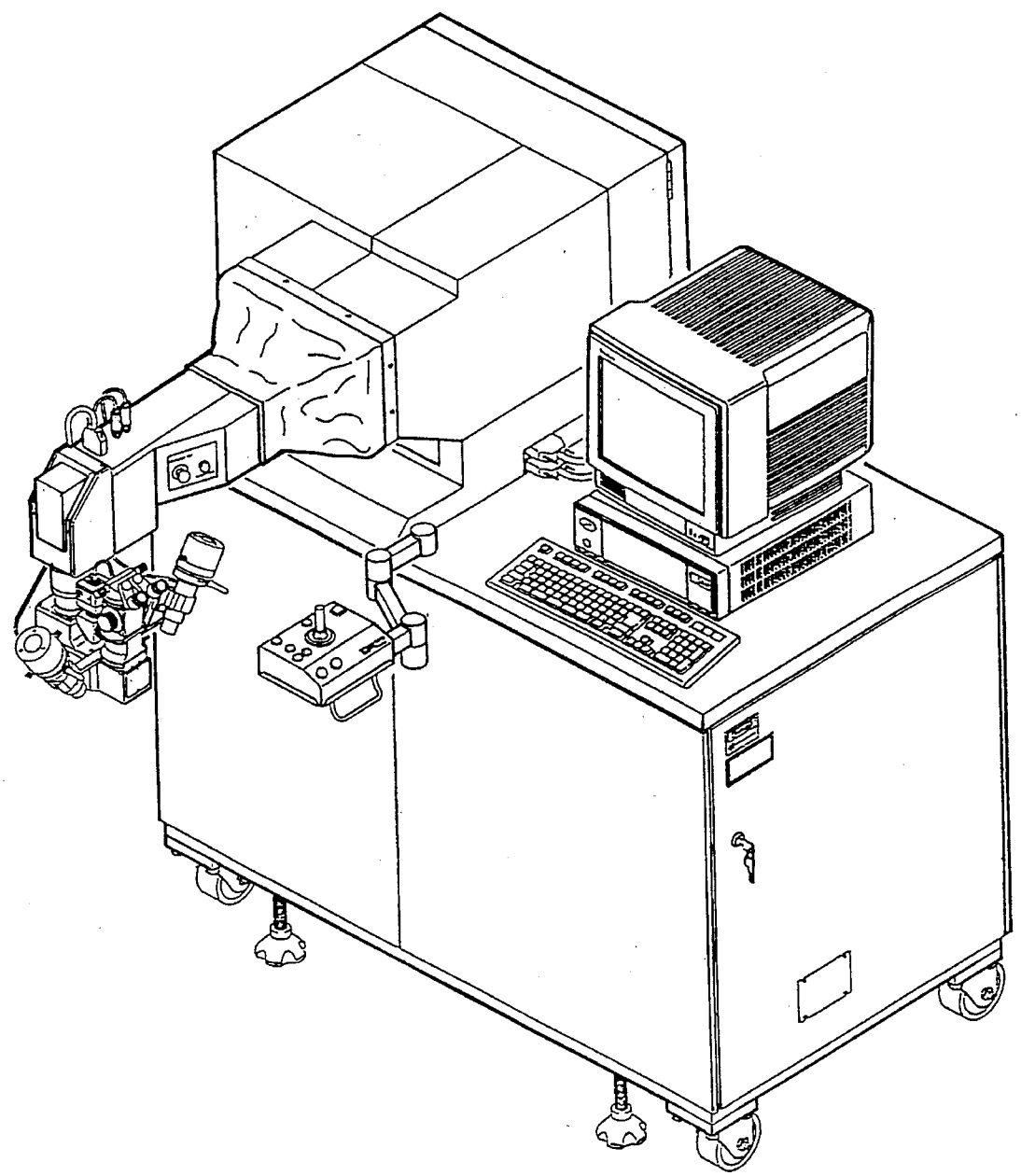
FIG. 4 is a perspective view of a cornea operation apparatus according to the present invention.

In FIG. 4, a cornea operation apparatus for correcting refractive error of a patient's eye is shown. The laser transmitting optical system of the apparatus has little relation to the present invention, accordingly the detail description thereof, having been mentioned in Japanese Patent Appl. No. HEI 2(1990)-416767 which corresponds to U.S. Appl. No. 812,819, is omitted in this specification. The only brief explanation thereof will be here described referring to FIG. 5.

Figure 5:
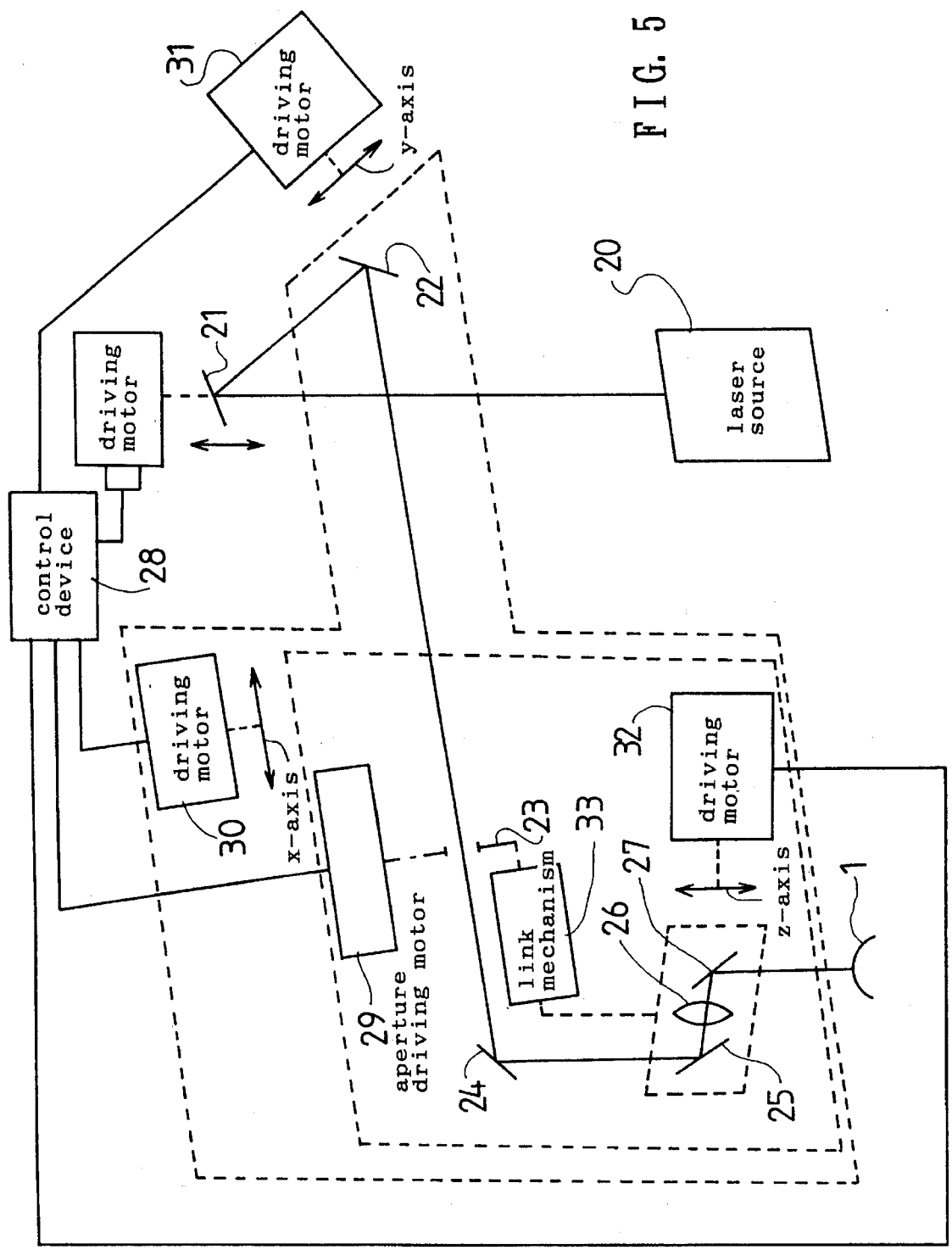
FIG. 5 is an arrangement diagram of laser transmitting optical system of the apparatus of FIG. 4.

As shown in FIG. 5, an optical system includes an ablating laser source 20 (preferably an excimer laser), plane mirrors 21, 22, 24, 25 and 27 for deflecting the laser beam emerging from the laser source 20, an aperture 23 located in the optical path between the mirrors 21, 22, 24, 25 and a projection lens 26, the projection lens 26 which is arranged in the optical path and for projecting the laser beam passing through the aperture 23 to a cornea of the examinee's eye 1 via mirror 27. The aperture 23 has a variable diameter which is changed by an aperture drive motor 29 in accordance with an instruction signal of a control device 28.

The projection lens 26 is conjugated with the aperture 23 and the cornea of the examinee's eye 1, and the laser beam passing through the aperture 23 in a confined space is projected on the surface of the cornea through the lens 26 such that an ablation area of the cornea is restricted. Then, the laser beam passing through the projection lens 26 is deflected toward the examinee's eye 1 by the mirror 27.

The examinee's eye 1 is provided at a position having a predetermined positioning relation for the apparatus.

In an alignment driving mechanism of the optical system of the cornea operation apparatus shown in FIG. 5, the optical system including the aperture 23, the plane mirrors 24, 25, 27 and the projection lens 26 is movable parallel to the x-axis by a driving motor 30, the above optical system including further the plane mirror 22 is movable parallel to the y-axis by a driving motor 31. In this moving operation, the projection lens 26 keeps a conjugating relation with the aperture 23 and the examinee's eye 1.

The optical system including the plane mirror 25, the projection lens 26 and the plane mirror 27 is movable parallel to the z-axis by a driving motor 32, then the aperture 23 is moved according to the movement of the optical system by a link device 33 so that the projection lens 26 may keep as always a conjugating relation with the aperture 23 and the eye 1.

FIG. 6 shows an optical arrangement of an alignment light projecting system and an alignment observing system provided in relation with the alignment driving mechanism shown in FIG. 5.

The alignment observing system provides a microscope 10 for observing the cornea 11 of the examinee's eye.

The alignment light projecting optical systems 12a and 12b are disposed symmetrically at both sides of the optical axis of the microscope 10, which are provided respectively with illumination lamps 13a, 13b, condenser lenses 14a, 14b for condensing the light emerging from the illumination lamps 13a, 13b, linear slit diaphragms 15a, 15b, and projection lenses 16a, 16b for projecting the light beam passing through the slit diaphragms 15a, 15b to the cornea 11. The projection lenses 16a, 16b are conjugated with the respective slit diaphragms 15a, 15b and the cornea 11.

The light beam passing through the slit diaphragm 15a in the slit space is projected on the surface of the cornea 11 such that the slit image by the slit diaphragm 15a is always formed at a focus point on the optical axis of the microscope 10. The light beam passing through the slit diaphragm 15b is similarly projected to the cornea 11.

The alignment operation with the apparatus including the above optical system will be explained as below.

For the alignment in the optical axis direction, the slit light beam emerging from the slit projecting optical system 12a (left side system in FIG. 6), although substantially passes through the cornea 11, is partially diffused by the cornea 11 toward the microscope 10, and thereby a slit line image 17a of circular arc shape is observed through the microscope 10 as shown in FIGS. 7(a) through 7(c). Similarly, the light beam emerging from the slit projecting optical system 12b (right side system in FIG. 6) is observed as a slit line image 17b of circular arc shaped through the microscope 10.

When the apex of the cornea 11 is placed at a focus position of the microscope 10, as shown in FIG. 7(a), the slit line image 17a and the slit line image 17b partially overlap each other at the apical point of the cornea. But then, when the cornea 11 is positioned below the position shown in FIG. 6, that is, far from the microscope 10 than the focus position of the microscope 10, two slit line images 17a and 17b are apart from each other as shown in FIG. 7(b). When the cornea 11 is positioned above the position shown in FIG. 6, that is, near the microscope 10 than the position on which the microscope 10 is focused, two slit line images 17a and 17b intersect as shown in FIG. 7(c).

Accordingly, when the two slit line images 17a and 17b are observed as FIG. 7(b), the apparatus is moved downward (to the z-axis direction in FIG. 5) or the cornea 11 upward so that a distance between the microscope 10 and the cornea 11 is made shorter, and, when the two slit line images 17a and 17b are observed as FIG. 7(c), the apparatus 10 is moved upward or the cornea 11 downward so that the distance is made longer. Thus, if adjusting the distance between the apparatus 10 and the cornea 11 such that the two slit line images 17a and 17b may be observed as FIG. 7(a), the alignment to focus the microscope 10 on the cornea 11 is accordingly completed.

Figure 8:
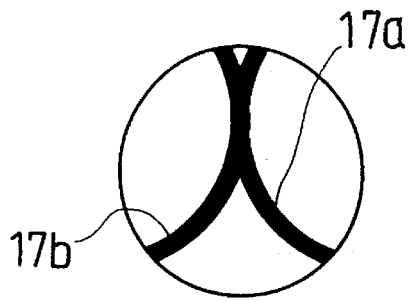
FIGS. 8(a) and 8(b) are diagrams of showing various alignment conditions in the longitudinal direction according to the present invention.
Figure 8:
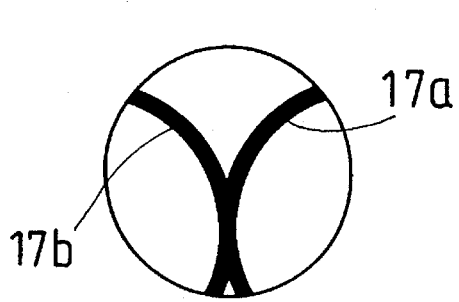
Figure 9:
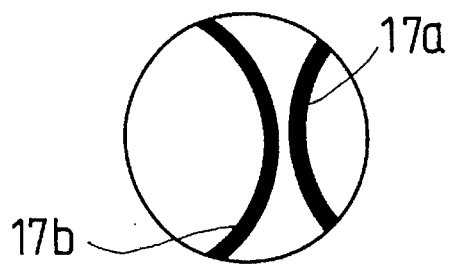
FIGS. 9(a) and 9(b) are diagrams of showing various alignment conditions in the lateral direction according to the present invention.
Figure 9:
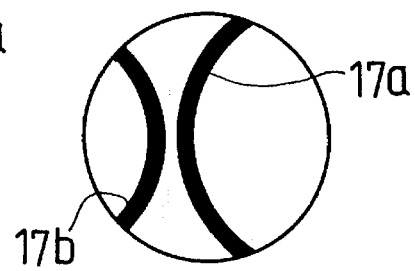

Next, in the alignment operation in the longitudinal and lateral directions, the two slit line images 17a and 17b are observed as in either FIG. 8(a) or FIG. 8(b) when the apex of the cornea is dislocated in the longitudinal direction of the visual field, and the two slit images 17a and 17b are observed as in either FIG. 9(a) and FIG. 9(b) when dislocated in the lateral direction. For this alignment, the cornea 11 and the optical axis of the microscope 10 are relatively moved so that the two slit line images 17a and 17b are placed at respective correct positions in the visual field as shown in FIG. 7(a).

More specifically, when the apex of cornea is dislocated in the longitudinal direction of the visual field, the apparatus is moved parallel to the y-axis of FIG. 5 or the cornea is moved in the longitudinal direction thereof. When the apex of cornea is dislocated in the lateral direction of the visual field, the apparatus is moved parallel to the x-axis of FIG. 5 or the cornea is moved in the lateral direction thereof.

Figure 10:
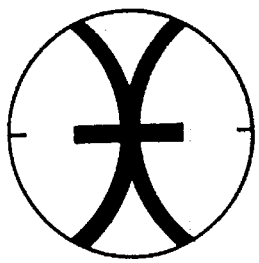
FIG. 10 is a diagram of showing an alignment condition with another slit diaphragm according to the present invention.

The present invention may be embodied in other specific forms without departing from the spirit or essential characteristics thereof. For instance, although the slit diaphragms 15a, 15b each provides a linear slit therein in the above embodiment, at least either slit diaphragm may further provide an across line in the center, referring to FIG. 10, which make the recognition which portion should be adjusted to a center of the visual field clearly and accordingly the alignment between the visual field and the cornea easily. Additionally, if the observing system is given a reticle indicating a position at which the across line should be placed, the alignment is made more easily.

Figure 11:
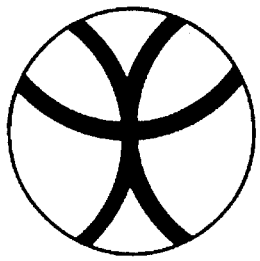
FIGS. 11(a) and 11(b) are diagrams of showing each alignment condition with another slit diaphragms according to the present invention.
Figure 11:
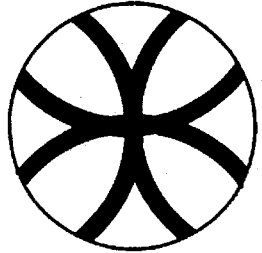

If, in addition to two linear slit line images, one or more slit line images are provided so as to overlap each other at a point as shown in FIGS. 11(a) and 11(b), the alignment can be easy achieved.

And further, the slit diaphragm in the present invention can have various slit forms without limited to a linear slit form.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus, comprising:

a first slit image projection system and a second slit image projection system for respectively projecting first and second alignment slits on an eye of a patient along first and second directions;

an apparatus body comprising a slit image observing system for observing on the eye the alignment slits projected by the first and second slit image projection systems; and an alignment moving means for 3-dimensionally moving said apparatus body relative to the patient's eye.

2. The ophthalmic apparatus of claim 1, wherein an optical axis of the slit image observing system is located in part, between the first and second directions.

3. The ophthalmic apparatus of claim 1, wherein each of said first and second slit image projection systems comprises a slit diaphragm having a slit, a light source for illuminating said slit diaphragm and a projection lens for projecting an alignment slit image on the eye.

4. The ophthalmic apparatus of claim 3, wherein said slit comprises a linear slit.

5. The ophthalmic apparatus of claim 4, wherein said slit diaphragm comprises another slit which extends across said linear slit.

6. The ophthalmic apparatus of claim 3, wherein said slit in said slit diaphragm further comprises a cross slit wherein said cross slit crosses said slit at a predetermined angle.

7. The ophthalmic apparatus of claim 1, further comprising an operation laser source and an operation laser optical system for projecting an operation laser beam from the laser source onto the eye.

8. The ophthalmic apparatus of claim 7, wherein each of said first and second slit image projection systems comprises a slit diaphragm having a slit, a light source for illuminating said slit diaphragm and a projection lens for projecting an alignment slit image on the eye.

9. The ophthalmic apparatus of claim 8, wherein said slit comprises a linear slit.

10. The ophthalmic apparatus of claim 9, wherein said slit diaphragm comprises another slit which extends across said linear slit.

11. The ophthalmic apparatus of claim 8, wherein said slit in said slit diaphragm further comprises a cross slit wherein said cross slit crosses said slit at a predetermined angle.

* * * * *